United States Patent [19]

Nelson, Jr. et al.

[11] Patent Number: 5,283,005
[45] Date of Patent: Feb. 1, 1994

[54] SYNERGISTIC BIOCIDE COMBINATION FOR INDUSTRIAL FLUIDS

[75] Inventors: John D. Nelson, Jr., Naugatuck; Jon R. Geiger, West Hartford, both of Conn.

[73] Assignee: Olin Corporation, Cheshire, Conn.

[21] Appl. No.: 957,833

[22] Filed: Oct. 8, 1992

[51] Int. Cl.$^5$ ............... C10M 129/00; C02F 1/00
[52] U.S. Cl. .................... 252/380; 210/764; 422/1
[58] Field of Search ........... 252/380, 403, 405, 400.62; 422/1; 210/764

[56] References Cited

U.S. PATENT DOCUMENTS

| | | | |
|---|---|---|---|
| 3,359,165 | 12/1967 | Bergy et al. | 424/119 |
| 3,595,956 | 7/1971 | Florestano | 514/11 |
| 4,149,983 | 5/1979 | Grier et al. | 252/51.5 R |
| 4,723,950 | 2/1988 | Lee | 604/322 |
| 4,957,658 | 9/1990 | French et al. | 252/400.23 |
| 5,120,711 | 6/1992 | Magyar et al. | 514/11 |

OTHER PUBLICATIONS

"Synergism between Chlorohexidine and Polymyxins against *Pseudomonas aeruginosa*" by A. R. Najjar and L. B. Quesnel, accepted Jun. 25, 1979 Journal of Applied Bacteriology 1979, pp. 469 through 476.

"Sensitization of Gram-negative bacteria to antibiotics and complement by a nontoxic oligopeptide" by Martti Vaara and Timo Vaara, Jun. 1983 Letters to Nature, vol. 303, pp. 526 through 528.

*Primary Examiner*—Robert L. Stoll
*Assistant Examiner*—Valerie Fee
*Attorney, Agent, or Firm*—Dale Lynn Carlson

[57] ABSTRACT

The present invention relates to a composition comprising a antimicrobially effective amount of a combination of an pyrithione and a lipopeptide antibiotic. Also disclosed is an aqueous industrial functional fluid comprising an aqueous base fluid medium and an antimicrobially effective amount of a combination of a pyrithione and a lipopeptide antibiotic. Also disclosed is a process for providing biocidal activity to an aqueous industrial functional fluid which comprises incorporating into said fluid an antimicrobially-effective amount of a combination of a pyrithione and a lipopeptide antibiotic.

9 Claims, No Drawings

SYNERGISTIC BIOCIDE COMBINATION FOR INDUSTRIAL FLUIDS

FIELD OF THE INVENTION

This invention relates generally to biocides and, more specifically to a synergistic combination of a pyrithione salt or acid and a basic lipopeptide antibiotic as a microbiostatic mixture for aqueous industrial functional fluids, such as metalworking fluids.

BACKGROUND OF THE INVENTION

Aqueous industrial functional fluids, such as metalworking fluids, are susceptible to the proliferation of microorganisms which can cause odors, deterioration, and corrosion. Antimicrobial additives (so-called preservatives) for the industrial fluids are needed to minimize the proliferation of the microorganisms. Preservatives that are effective at low doses, biodegradable, and relatively non-toxic, are desirable for environmental and economic reasons.

Pyrithione is a well-known biocide enjoying substantial commercial use as an antimicrobial agent in aqueous industrial functional fluids, such as metalworking fluids, lubricants, textile sizes, ink jet printing fluids, and the like. Sodium pyrithione and zinc pyrithione are widely employed as biodegradable fungistats in aqueous coatings, fiber lubricants, plastics, adhesives, and metalworking fluids as illustrated by the disclosures contained in U.S. Pat. No. 4,957,658.

Various basic lipopeptide antibiotics are also known, such as polymyxin B, colistin (also called polymyxin E), and octapeptin are known in the art. The primary use of these antibiotics is to treat superficial infections, as disclosed, for example, in U.S. Pat. No. 5,120,711. More specifically, the '711 patent discloses the use of antibiotics, such as polymyxin B, in combination with clotrimazole or chlorquinaldol in the preparation of synergistically active veterinary compositions useful for the treatment of mastitis and metritis. In addition, certain of these antibiotics have been disclosed as being useful in metalworking fluids, as disclosed, for example, in U.S. Pat. No. 3,359,165.

Heretofore, the combination of pyrithione and lipopeptide antibiotics has not been known for any purpose, much less in the preparation of a antimicrobial mixture exhibiting enhanced biocidal efficacy for aqueous industrial functional fluids, such as metalworking fluids. Such a antimicrobial mixture would be highly desired by the industrial fluids manufacturing community.

SUMMARY OF THE INVENTION

In one aspect, the present invention relates to a composition comprising an antimicrobially effective amount of a combination of a pyrithione and a lipopeptide antibiotic.

In another aspect, the present invention relates to an aqueous industrial functional fluid comprising an aqueous base fluid medium and an antimicrobially effective amount of a combination of a pyrithione and a lipopeptide antibiotic.

In another aspect, the present invention relates to a process for providing biocidal activity to an aqueous industrial functional fluid which comprises incorporating into said fluid an antimicrobially-effective amount of a combination of a pyrithione and a lipopeptide antibiotic.

These and other aspects will become apparent upon reading the following detailed description of the invention.

DETAILED DESCRIPTION OF THE INVENTION

It has now been surprisingly found in accordance with the present invention that a composition comprising a combination of pyrithione with a lipopeptide antibiotic provides synergistic biocidal effectiveness. As use herein, the term "synergistic antimicrobial effectiveness" means that the composition exhibits greater antimicrobial activity than the additive amounts of activity provided when each component of the combination is employed alone. The composition exhibits synergistic antimicrobial activity with respect to the growth of microorganisms, notably bacteria and fungi. The antimicrobial activity is provided during use of the composition, for example, in an aqueous industrial functional fluid composition, such as a metalworking fluid, lubricant, or diagnostic reagent for immunological testing, in order to provide biocidal protection against microbes such as bacteria and fungi during use of the fluid.

The pyrithione used in the process and composition of this invention is preferably a pyrithione salt, such as sodium pyrithione, zinc pyrithione, chitosan pyrithione, magnesium disulfide pyrithione, copper pyrithione, and the like, although pyrithione acid can be used if desired. More preferable pyrithione salts include sodium pyrithione, copper pyrithione, and zinc pyrithione, most preferably sodium pyrithione.

The lipopeptide antibiotic useful in the present invention is suitably any such antibiotic, such as, for example, polymyxin B, polymyxin E (also referred to as colistin), octapeptin, combinations thereof, and the like. The preferred antibiotic is polymyxin B, which is commercially available and is preferably utilized in the present invention in the form of the sulfate salt of polymyxin B. As used herein, the term "polymyxin B" refers to polymyxin B and to its antimicrobial derivatives such as the hydrochloride, sulfate, palmitate, methanesulfonate and oxalate salts. The anionic moieties of such salts do not substantially affect the synergistic antimicrobial activity of the compositions of the invention, and such salts can be employed advantageously therein.

The weight ratio of pyrithione to antibiotic employed in the compositions of the present invention is preferably between about 1:30 and about 700:1, more preferably between about 1:1 and about 100:1. The pyrithione and antibiotic is employed in a total amount sufficient to provide at least a microbiostatically effective concentration in the composition in which they are utilized. Preferably, the pyrithione and the antibiotic are each employed in the composition in an amount of between about 0.1 and about 1,000, more preferably between about 1 and about 1000 ppm for the pyrithione and between about 0.1 and about 100 ppm for the polymyxin. If the composition is a metalworking fluid composition, it is preferred that water be present in the composition in an amount of at least about 80 weight percent, preferably at least about 90 weight percent, based upon the total weight of the composition.

The novel compositions of the present invention are useful as disinfectants and preservatives, in a liquid or spreadable solid form, alone or in combination with an inert carrier such as water, liquid hydrocarbons, ethanol, isopropanol, or the like. They can be employed using conventional procedures to control bacteria and fungi in various substrates, and can be applied to bacterial or fungal organisms or their substrates in an antimicrobial amount by conventional procedures such as spraying, dipping, drenching impregnation, and the like.

EXAMPLE 1

Determinations of minimum inhibitory concentrations (MIC's) of the two compounds (pyrithione salts and/or polymyxin sulfate) in a nutrient broth (alone and in mixtures) were conducted to evaluate interactions. Stock solutions of pyrithione salts and/or polymyxin sulfate were diluted in Tryptic Soy Broth (Difco), and the dilutions were inoculated with an equal volume of bacterial culture ($10^6$/ml) or fungal spore suspension ($10^5$/ml) in Tryptic Soy Broth and incubated at 28° C. for 3-7 days. The highest dilution free of growth was determined to be the MIC, as given in Table 1 below.

The interaction of the antimicrobials was determined according to an accepted procedure (M. C. Berenbaum). The concentration of each agent in the combination that inhibits the organisms is expressed as a fraction of the concentration that causes the same effect when the same agent is tested alone (i.e., its fractional inhibitory concentration, FIC). If the sum of the FIC's is 1, the combination is additive in its antimicrobial effect; if the sum is <1, the combination is synergistic; and if the sum is >1, the combination is antagonistic. According to this criterion, mixtures of sodium pyrithione and polymyxin acted in synergism against 15 of 18 bacteria and fungi, resulting in 2-to 32-fold reductions in MIC's relative to the pure compounds over a range of sodium pyrithione to Polymyxin of 1/20 to 650/1 (Table 1).

Similarly, zinc pyrithione acted in synergism with polymyxin against 12 of 18 bacteria and fungi, with 2- to 32-fold reductions in MIC's using a range of zinc pyrithione to polymyxin ratios of 1/32 to 256/1 (Table 2).

TABLE 1

SYNERGISM OF SODIUM PYRITHIONE (SP) POLYMYXIN B (PB) MIXTURES

| Organism[b] | Minimum Inhibitory Concentration (ppm)[a] | | | | SP[c] PB | Sum of Fractional Inhibitory Concentrations[d] |
|---|---|---|---|---|---|---|
| | Compounds Used Alone | | Mixture | | | |
| | SP | PB | SP | PB | | |
| BACTERIA: | | | | | | |
| Pseudomonas Stutzeri | 81.3 | 0.3 | 40.6 | 0.1 | 325-650 | 0.75 |
| Pseudomonas fluorescens | 135.5 | 10.7 | 6.7 | 1.2 | 3-10 | .16 |
| Citrobac.·ia frenndii | 12.7 | 0.5 | 6.7 | 0.1 | 41-81 | 0.75 |
| Pseudomonas oleovorans | 12.7 | 0.3 | 3.2 | <0.1 | 41-163 | 0.50 |
| Pseudomonas rubescens | 23.7 | <0.1 | 2.5 | <0.1 | 650 | 0.52 |
| Alcaligens faecalis | 30.5 | 1.4 | 9.3 | 0.5 | 5-41 | 0.87 |
| Pseudomonas aeruginosa | 162.6 | 0.7 | 81.3 | 0.3 | 163-325 | 1.08 |
| Proteus mirabilis | 325.1 | >2048.0 | 61.0 | 288.0 | 1/20-1 | <0.33 |
| FUNGI: | | | | | | |
| Candida albicans | 33.9 | 256.9 | 6.7 | 64.0 | 1/20-1/10 | 0.46 |
| Trichophyton mentagrophytes | 20.3 | 32.0 | 8.5 | 26.7 | 1/10-½ | 1.25 |
| Aspergillus niger | 121.9 | 1536.0 | 40.6 | 256.0 | 1/10 | 0.57 |
| Penicillin pinophilium | 20.3 | 256.0 | 5.1 | 48.0 | 1/20-1/10 | 0.44 |
| Aureobasidium pullulans | 15.2 | 256.0 | 5.1 | 48.0 | 1/20-1/10 | 0.57 |
| Gliocladium virens | 108.3 | 74.7 | 15.2 | 21.3 | 1/10-1 | 0.51 |
| Chaetomium globosium | 12.7 | 24.0 | 3.8 | 16.0 | 1/10-1/5 | 1.13 |
| Fusarium solani | 243.8 | 128.0 | 40.6 | 32.0 | 1 | 0.44 |
| Fusarium sp. | 243.8 | 128.0 | 40.6 | 32.0 | 1 | 0.44 |
| Cephalosporium sp. | 50.8 | 256.0 | 15.2 | 12.0 | 1 | 0.42 |

[a]Compounds were serially diluted in Tryptic soy Broth (DIFCO), inoculated and incubated at 28° C. Average of two to four determinations. Active ingredients basis. PB 7610 units/mg.
[b]Each dilution contained $10^6$ bacteria/ml of $10^5$ fungi/ml. Bacteria were incubated 3 days and fungi were incubated 6-7 days.
[c]Ratio of Sodium pyrithione to Polymyxin B sulfate in mixture
[d]Criterion of synergism according to Berenbaum (1). Mixture is synergistic if sum <1 (avg. of two to four determinations).

TABLE 2

SYNERGISM OF ZINC PYRITHIONE (ZP) POLYMYXIN B (PB) MIXTURES

| Organism[b] | Minimum Inhibitory Concentrations (ppm)[a] | | | | ZP[c] | Sum of Fractional Inhibitory Concentrations[d] |
|---|---|---|---|---|---|---|
| | Compound Used Alone | | Mixture | | | |
| | SP | PB | SP | PB | PB | |
| BACTERIA: | | | | | | |
| Pseudomonas Stutzeri | 4.0 | 0.3 | 4.0 | <0.1 | 16–128 | 1.04 |
| Pseudomonas fluorescens | 106.7 | 6.7 | 4.7 | 0.4 | 0.11 | 0.16 |
| Citrobacteria freundii | 8.0 | 0.4 | 3.3 | 0.1 | 16–64 | 0.71 |
| Pseudomonas oleovorans | 6.7 | 0.5 | 4.0 | 0.2 | 16–32 | 1.00 |
| Pseudomonas rubescens | 3.3 | <0.1 | 3.3 | <0.1 | 256 | 1.42 |
| Alcaligens faecalis | 10.7 | 3.3 | 6.7 | 0.6 | 8–32 | 0.85 |
| Pseudomonas aeruginosa | 288.0 | 1.0 | 112.0 | 0.5 | 128–256 | 1.19 |
| Proteus mirabilis | 4.0 | >2048.0 | 2.0 | 64.0 | 1/32 | <0.53 |
| FUNGI: | | | | | | |
| Candida albicans | 8.0 | 341.3 | 4.0 | 74.7 | ¼–1/32 | 0.75 |
| Trichophyton mentagrophytes | 8.0 | 53.0 | 8.0 | 26.7 | ¼–½ | 1.58 |
| Aspergillus niger | 32.0 | 1024.0 | 16.0 | 298.7 | 1/32–⅛ | 0.79 |
| Penicillin pinophilium | 16.0 | 128.0 | 4.0 | 32.0 | ¼ | 0.50 |
| Aureobasidium pullulans | 8.0 | 288.0 | 4.0 | 80.0 | 1/32–1/16 | 0.84 |
| Gliocladium virens | 80.0 | 64.0 | 24.0 | 20.0 | 1–2 | 0.69 |
| Chaetomium globosium | 6.7 | 26.7 | 2.7 | 13.3 | ¼–½ | 1.00 |
| Fusarium solani | 64.0 | 85.3 | 13.3 | 37.3 | ½–1 | 0.75 |
| Fusarium sp. | 64.0 | 106.7 | 18.7 | 42.7 | ½–1 | 0.79 |
| Cephalosporium sp. | 16.0 | 170.7 | 4.0 | 42.7 | 1/16–¼ | 0.54 |

[a]Stock solutions of ZP in dimethylsulfoxide and PB in sterile water were serially diluted in Tryptic Soy Broth (DIFCO), inoculated and incubated at 28 C. Average of two to four determinations. Active ingredient basis. PB 7730 units/mg.
[b]Each dilution contained $10^6$ bacteria/ml or $10^5$ fungi/ml. Bacteria were incubated 6 days, and fungi were incubated 7 days.
[c]Ratio of ZP to PB sulfate in mixture.
[d]Criterion of synergism according to Berenbaum (1). Mixture is synergistic if sum < 1. (Avg. of two to four determinations).

TABLE 3

EFFICACY OF SODIUM PYRITHIONE - POLYMYXIN B MIXTURES IN SYNTHETIC METALWORKING FLUIDS[a]

| Experiment | Fluid[c] | Sodium Pyrithione (SP)[b] | | Polymyxin (PB)[b] | | | SP | Mixture[b] (ppm) | | | |
|---|---|---|---|---|---|---|---|---|---|---|---|
| | | 83 ppm | 8.3 ppm | 50 ppm | 10 ppm | 5 ppm | PB | 8.3 / 5.0 | 4.2 / 5.0 | 2.0 / 5.0 | 2.0 / 1.3 |
| 1[d] | 1 | — | 2.3 | — | — | 0.0 | | >3.8 | — | — | 3.0 |
| 2[d] | 1 | — | 1.9 | — | — | 0.0 | | >4.2 | >4.2 | >4.2 | — |
| 3[e] | 2 | >6.7 | 2.4 | 1.9 | — | 2.8 | | >6.7 | — | — | — |
| 4[d] | 3 | 0.5 | — | — | 1.1 | — | | >3.9 | — | — | — |

[a]$Log_{10}$ reduction in total bacterial and fungal plate count relative to untreated control after 22-28 days at 28° C. in 5% aqueous fluids shaken in Erlenmeyer flasks.
[b]Concentration (active ingredients basis) in 5% aqueous (i.e., a 5 wt % of metalworking fluid concentrate in water) dilution of metalworking fluid concentrate. Polymyxin B: 7610 units/mg.
[c]Fluid #1 (CITCOOL 33 ™), a metalworking fluid concentrate manufactured by Citgo Petroleum Corp., contains polyalkylene glycol (5–10%), alkanolamine (15–22%), an oxygenated aliphatic hydrocarbon (7–12%), disodium dimercaptothiadiazole (1–4%), and water (65–70%); fluid #2 is a metalworking fluid concentrate manufactured by Pacer Lubricants; and fluid #3 is a metalworking fluid concentrate consisting of triethanolamine (15%), pelargonic acid (10%), an amine-borate salt (7%), a carboxylic acid-alkanolamine salt (2%), and water (66%).
[d]Challenged with mixture of fungal metalworking fluid isolates ($10^5$ spores per ml of fluid), including Cephalosporium sp., Fusarium sp., and Fusarium solani IMI 314228.
[e]Fluid contaminated with an initial level of $5.5 \times 10^4$ bacteria and fungi per ml.

Mixtures also proved to be more active than the pure compounds in aqueous synthetic metalworking fluids, as identified in Table 3 above. Virgin fluids (5%) were challenged with fungi and incubated at 26° C. in shaken Erlenmeyer flasks. In one case (fluid #2, Table 3), fluid naturally contaminated with bacteria and fungi in the field was used. Samples were withdrawn at weekly intervals, and numbers of viable organisms were enumerated after incubation in Tryptic Soy Agar (Difco) at 28° C. for 4–5 days. Sodium pyrithione-polymyxin mixtures (approx. 2/1 to ⅓) produced 10-to 10,000-fold greater reductions in contaminant levels than either component used alone at the same concentrations.

While the invention has been described above with references to specific embodiments thereof, it is apparent that many changes, modifications and variations in the materials, arrangements of parts and steps can be made without departing from the inventive concept disclosed herein. Accordingly, the spirit and broad scope of the appended claims is intended to embrace all such changes, modifications and variations that may occur to one of skill in the art upon a reading of the disclosure. All patent applications, patents and other publications cited herein are incorporated by reference in their entirety.

Having thus described the invention, what is claimed is:

1. A composition for controlling bacteria and fungi comprising an aqueous based industrial fluid medium and an antimicrobially effective amount of a combination of a pyrithione and a lipopeptide antibiotic, said lipopeptide antibiotic being selected from the group consisting of polymyxin B, polymyxin E, octapeptin, and combinations thereof, said pyrithione being selected from the group consisting of sodium pyrithione, zinc pyrithione, chitosan pyrithione, magnesium disulfide pyrithione, copper pyrithione, pyrithione acid, and combinations thereof, and said antibiotic being employed in said composition in weight ratio of pyrithione to antibiotic of between about 1:30 and about 700:1.

2. The composition of claim 1 wherein said pyrithione and said antibiotic are employed in said composition in a weight ratio of pyrithione to antibiotic of between about 1:1 and about 100:1.

3. The composition of claim 1 which further comprises an inert carrier.

4. The composition of claim 1 wherein said pyrithione and said antibiotic are each employed in said composition in an amount of between about 0.1 ppm and about 1000 ppm.

5. A process for providing biocidal activity to an aqueous industrial functional fluid which comprises incorporating into said fluid an antimicrobially-effective amount of a combination of a pyrithione and a lipopeptide antibiotic.

6. The process of claim 5 wherein said pyrithione and said antibiotic are employed in said fluid in a weight ratio of pyrithione to antibiotic of between about 1:30 and about 700:1.

7. The process of claim 5 wherein said pyrithione and said antibiotic are employed in said fluid in a weight ratio of pyrithione to antibiotic of between about 1:1 and about 100:1.

8. The process of claim 5 wherein said fluid additionally comprises an inert carrier.

9. The process of claim 5 wherein said pyrithione and said antibiotic are each employed in said fluid in an amount of between about 0.1 ppm and about 1000 ppm.

* * * * *